US00PP13283P2

(12) United States Plant Patent
Osiecki

(10) Patent No.: US PP13,283 P2
(45) Date of Patent: Nov. 26, 2002

(54) SPATHIPHYLLUM PLANT NAMED 'STWENTYNINE'

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 09/933,236

(22) Filed: Aug. 20, 2001

(51) Int. Cl.[7] ..... A01H 5/00
(52) U.S. Cl. ..... Plt./364
(58) Field of Search ..... Plt./364

*Primary Examiner*—Bruce R. Campell
*Assistant Examiner*—A Para

(57) ABSTRACT

A new and distinct cultivar of Spathiphyllum is provided. It is a large, relatively narrow plant, suitable for production in 20-cm and larger containers, with vigorous growth; upright and symmetrical growth habit; large, thick, ribbed, dark green and glossy leaves. Very large spathes are held relatively close to foliage on thick, strong, straight peduncles.

2 Drawing Sheets

BOTANICAL CLASSIFICATION

Spathiphyllum hybrid.

VARIETY DENOMINATION

'Stwentynine'.

BACKGROUND OF THE INVENTION

This invention relates to a new and distinct cultivar of spathiphyllum plant, botanically known as Spathiphyllum hybrid, and hereinafter referred to by the cultivar name Stwentynine.

The new cultivar is a product of a planned breeding program conducted by the Inventor in Altha, Fla. The objective of the program was to develop a large, fast growing, Spathiphyllum cultivar useful for various container sizes with attractive growth habit and large, dark green and glossy leaves.

The new Spathiphyllum was discovered and selected by the Inventor in 1997 as a seedling within the progeny of a cross made in 1996 in a controlled environment in Altha, Fla. The female parent was Spathiphyllum hybrid cultivar S17, disclosed in U.S. Plant Pat. No. 10,807 a/k/a Spathiphyllum 1998™. The male parent was the proprietary Spathiphyllum seedling selection identified by the code number 93-8-1, obtained in the same program, not patented.

Asexual propagation of 'Stwentynine' since 1998 by means of tissue culture in Altha, Fla. has established that the unique characteristics of this new cultivar are in fact stable and reproduced true to type in successive generations.

SUMMARY OF THE INVENTION

The new Spathiphyllum cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Stwentynine' as a new and distinct cultivar of Spathiphyllum:

1. Large size, tall plant, appropriate for 20-cm and larger containers;

2. Symmetrical, upright, relatively open growth habit;

3. Very vigorous growth;

4. Large, wide, thick, ribbed, dark green and glossy leaf blades;

5. Spathes held relatively close to foliage on very thick, strong, straight, vertical peduncles;

6. Very large spathes with green veins and some yellowish coloration on back side;

7. Large spadices.

Plants of 'Stwentynine' are distinguished from plants of the female parent, cultivar S17, by its greater height; more upright, narrower and more open growth habit; more vigorous growth; less abundant branching and flowering; larger, darker green and glossier leaf blades; spathes that are longer, with more yellowish and green coloration on the back side and are held closer to foliage on thicker and stronger peduncles.

Plants of 'Stwentynine' are distinguished from plants of the male parent, seedling 93-8-1 by its narrower, more upright growth habit, less abundant flowering, longer petiole wings, leaf blades shorter with lower length to width ratio; spathes held closer to foliage on shorter, thicker and stronger peduncles.

The new cultivar can be compared to the known cultivars: Spathiphyllum 'Gorgusis No. 1', disclosed in U.S. Plant Pat. No. 6,964, a/k/a Sensation® and Spathiphyllum Supreme® (not patented).

Plants of the new Spathiphyllum cultivar differ from plants of Spathiphyllum Gorgusis No. 1 in the following characteristics:

1. Plants of 'Stwentynine' have narrower and more upright growth habit than plants of 'Gorgusis No. 1' and are suitable for 20-cm and larger containers, whereas pants of 'Gorgusis No. 1' are suitable for 25-cm and larger containers.

2. Leaf blades of 'Stwentynine' are smaller, with lower length to width ratio and glossier than leaf blades of 'Gorgusis No. 1'.

3. Petioles of 'Stwentynine' are thinner and have narrower, less prominent petiole wings than petioles of 'Gorgusis No. 1'.

4. Peduncles of 'Stwentynine' are thicker and stronger than peduncles of 'Gorgusis No. 1'.

5. Spathes of 'Stwentynine' have more yellowish and green coloration on the back side than spathes of 'Gorgusis No. 1'.

Plants of the new Spathiphyllum cultivar differ from plants of Spathiphyllum Supreme in the following characteristics:

1. Plants of 'Stwentynine' have more upright and symmetrical growth habit, are taller and narrower than plants of Supreme.
2. Plants of 'Stwentynine' branch and flower less readily than plants of Supreme.
3. Leaf blades of 'Stwentynine' are larger, with lower length: width ratio, more ribbed, darker green and glossier than leaf blades of Supreme.
4. Petioles of 'Stwentynine' are much thicker, have shorter and thicker geniculum and more prominent petiole wings than petioles of Supreme.
5. Spathes of 'Stwentynine' are held closer to foliage on thicker and stronger peduncles than spathes of Supreme.
6. Spathes of 'Stwentynine' are larger, with greater length: width ratio and elliptic, whereas spathes of Supreme are between broadly ovate, oval and orbicular.
7. Spathes of 'Stwentynine' have more yellowish and green coloration on the back side than spathes of Supreme.
8. Spadices of 'Stwentynine' are larger and have larger pistils than spadices of Supreme.
9. Plants of 'Stwentynine' produce pollen very rarely, whereas plants of Supreme readily produce pollen.

BRIEF DESCRIPTION OF THE PHOTOGRAPHS

The accompanying photographs illustrate the appearance of the new Spathiphyllum cultivar, showing the colors as true as it is reasonably possible in color reproductions of this type. Colors in the photographs may appear slightly different from the color values cited in the botanical description, which accurately describe the actual colors of the plants of the new cultivar. The plant of 'Stwentynine' depicted in the photographs was approximately 15 months from planting a single tissue culture-produced microcutting, and was grown in a 25-cm container.

In the photographs:

BOTANICAL DESCRIPTION OF THE NEW CULTIVAR

Figure 1:
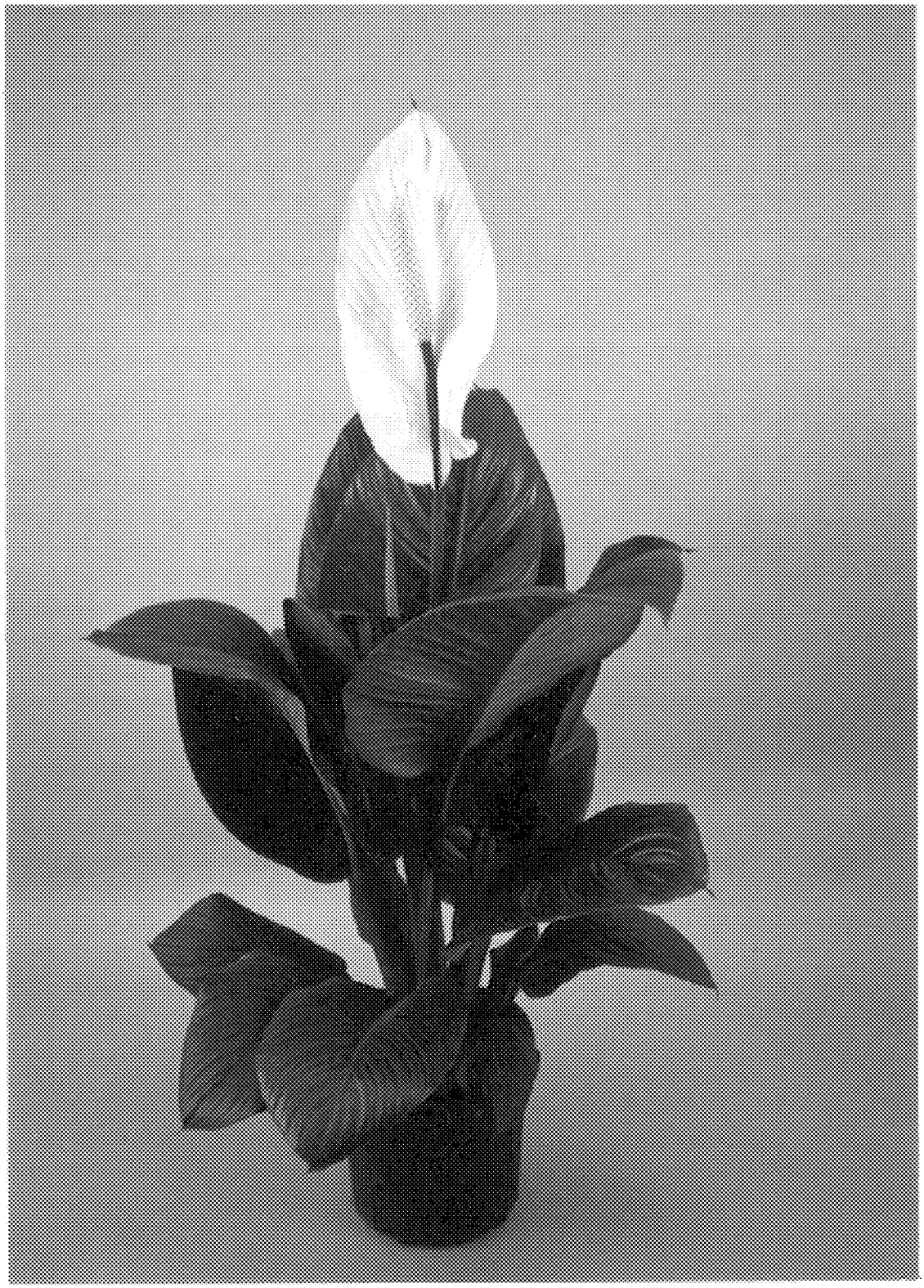
FIG. 1 depicts the whole plant.
Figure 2:
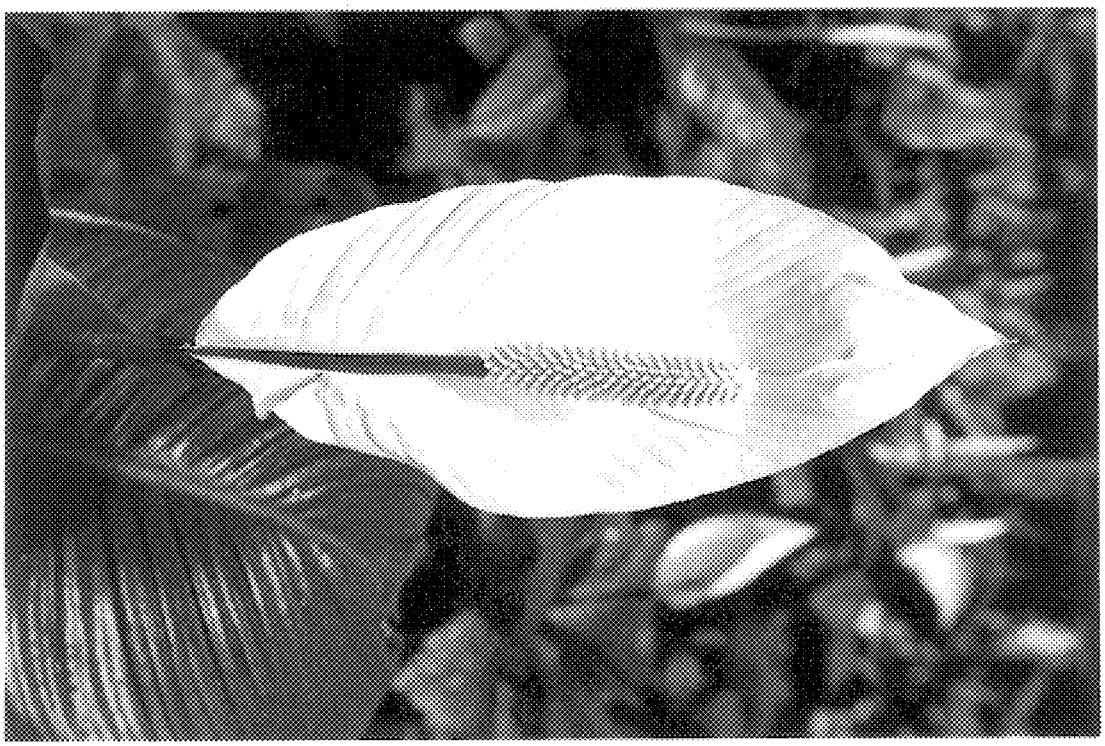
FIG. 2 illustrates the mature inflorescence.
Figure 3:
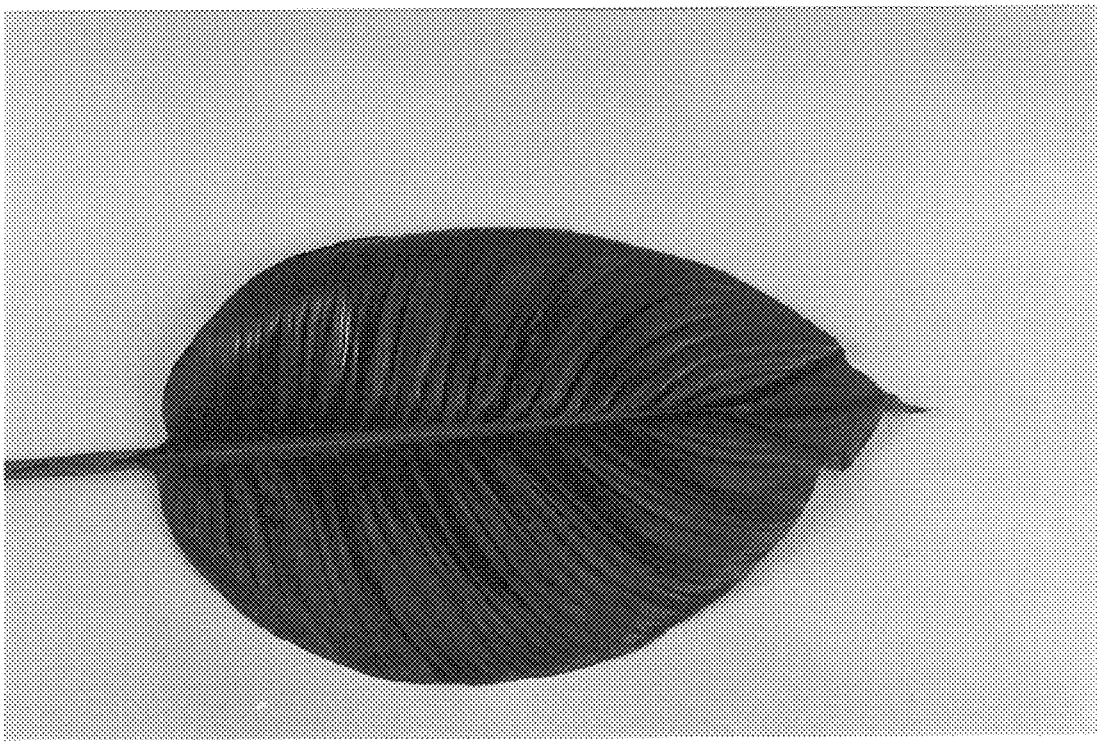
FIG. 3 illustrates the adaxial side of a mature leaf.

The following observations and measurements were recorded in July 2000, on plants grown in Homestead, Fla. in a commercial shadehouse covered with polypropylene shade cloth providing light reduction of 80% of ambient light level. During growth of these plants day temperature in the shadehouse ranged between 15° C. and 41° C., night temperature ranged between and 10° C. and 31° C., and light level ranged between 800 and 2200 foot-candles. Plants used for these observations were grown as single plants in 25-cm containers and were about 15 months from planting tissue culture-produced microcuttings.

Mature, fully developed plant organs were used for the following observations and measurements unless otherwise indicated. Fourth unrolled leaf from the top was used for mature leaf description. Numerical measurements represent means from typical plants of 'Stwentynine'. Color references are made to the R.H.S. Colour Chart, except where general color terms of ordinary significance are used. Color values were determined under natural light of approximately 900 to 1300 foot-candles.

Botanical classification: Spathiphyllum hybrid cultivar Stwentynine.

Parentage:

*Female parent.*—Spathiphyllum hybrid cultivar S17, disclosed in U.S. Plant Pat. No. 10,807, a/k/a Spathiphyllum 1998™.

*Male parent.*—Proprietary Spathiphyllum seedling selection identified by the code number 93-8-1, not patented.

Propagation:

*Type.*—Plant tissue culture.

*Time to produce a rooted liner.*—Summer: About 12 weeks at about 25 to 30° C. soil temperature. Winter: About 14 weeks at about 22 to 27° C. soil temperature.

Plant description:

*Growth habit.*—Tall, relatively narrow plant, with upright, symmetrical growth habit. Appropriate for 20-cm and larger containers.

*Plant size.*—Height, soil level to top of inflorescences: About 101.4 cm. Height, soil level to top of leaf canopy: About 83.9 cm. Diameter: About 74.5 cm.

*Plant vigor.*—Very vigorous.

*Crop time.*—About 14 months are needed to produce a finished plant in a 25-cm container from a single tissue culture-produced microcutting.

Foliage description:

*Petiole.*—Size: About 37.8 cm long, about 10.7 mm in diameter immediately below geniculum. Geniculum: About 5.4 cm long, about 12.1 mm in diameter at the base. Petiole wings: Prominent, extend along entire petiole length till juncture with leaf blade; usually folded adaxially, so that adaxial side of petiole and petiole wings not exposed. About 1.5 cm wide immediately below apex and about 2.1 cm wide mid-length. Color: Newly unrolled leaf, abaxial: Geniculum similar to 147B or between 147A and 147B; immediately below geniculum petiole color varies between different combinations of 147A and 146A; proximally lighter and more yellow. Petiole wings' apices between 147A and 147B; wings color near geniculum base similar to 147B; proximally lighter and more yellow, similar to 144B at the juncture with petiole sheath of a previous leaf. Mature leaf, abaxial: Usually darker and greener than 147A. Petiole wings darker than 147A, except for apices (147A).

*Leaf blade.*—Shape: Between broadly ovate and oval; apex acuminate with some cuspidate and aristate tendencies, often twisted; base variable, between obtuse and truncate with some cuneate tendencies, asymmetric; base directly connects with petiole wing at least on one side; margin entire, slightly wavy. Size: Mature leaf, fourth from top, about 45.5 cm long, about 28.6 cm wide; length: width ratio about 1.6 to 1. Young leaf, second from top, about 47.9 cm long, about 29.9 cm wide; length: width ratio about 1.6 to 1. Orientation: Upright; proximal approximately half of midrib of a fourth unrolled leaf from top at about 20° angle from vertical; distal half slightly curves outwards. Older leaves slightly more outwardly arching. Surface: Ribbed, slightly wavy. Texture: Thick, leathery, glabrous, glossy; young leaves very glossy. Venation: Pinnate, prominent; midrib deeply sunken in adaxial surface and protrudes from abaxial surface; primary veins are sunken in adaxial surface and protrude from abaxial surface. Color: Newly unrolled leaf, adaxial: Half that unrolls first similar to 147A near margin, lighter and more yellow near midrib. Half that unrolls last more yellow than 137A and more green than 146A. Midrib between 146A and 146B near base, distally slightly darker. Primary veins similar to or slightly lighter than surrounding tissue. Newly unrolled leaf, abaxial: Half that unrolls first between 147A and 147B. Half that unrolls last similar to 147B. Midrib near base between 146C and 144B in the center and between 147B and 146B on the sides; distally lighter and more yellow, between 145A and 144B at mid-length; in the most distal zone midrib is limited to fine line similar to 146A. Primary veins between 146C and 144B near midrib, and between 146A and 147A near margin. Mature leaf, adaxial: Much darker than 147A. Midrib similar to 147A. Primary veins slightly lighter than surrounding tissue. Mature leaf, abaxial: Similar to or slightly lighter and more silver gray than 147A. Midrib similar to 147B near leaf base; distally lighter and more yellow, similar to 144A in the middle, and limited to a fine line between 147A and 146A in the most distal zone. Primary veins similar to 144A near midrib, and to 147A near margin.

Inflorescence description:

*Inflorescence arrangement.*—Spathes with spadices held relatively close to foliage on straight, almost vertical, very thick and strong peduncles. Spathes cupped and approximately vertical through senescence. Spadices approximately vertical or slightly leaning forward and/or to the side.

*Flowering.*—Starts flowering naturally in spring in 20-cm or 25-cm containers about 14 months after planting tissue culture-produced microcuttings. At 15 months up to one inflorescence per plant.

*Spathe longevity.*—In summer spathe remains white for approximately 3 weeks following bud appearance and then gradually changes to a green color. Both spathe and spadix become conpletely green within 6 weeks following bud appearance.

*Peduncle.*—Size: About 81.1 cm long and about 10.3 mm in diameter immediately below spathe. Stipe about 2.2 cm long and 9.3 mm in diameter. Color, front: Between 147A and 147B immediately below spathe; proximally slightly more yellow (darker than 146A at petiole sheath juncture). Between spathe base and spadix base approximately 147A with some lighter streaks (approximately 144A) on the stipe. Color, back: Between 147A and 147B at juncture with stipe; proximally slightly more yellow (darker than 146A at petiole sheath juncture).

*Spathe.*—Shape: Elliptic; apex acuminate with aristate tendencies, twisted; base varies from almost obtuse with cuneate tendencies to almost cuneate with obtuse tendencies, asymmetric, often with one lobe forming a pocket; margin entire. Size: About 28.3 cm long, about 13.3 cm wide; length to width ratio about 2.1:1. About 4.5 cm deep. Surface: Usually wavy, especially in proximal zone; usually with irregular folds and pleats. Texture: Thick, leathery, glabrous, with pearl luster. Color: Closed bud: 155A or slightly darker, especially near midrib, where it may be between 155A and 4D. Mature spathe, front surface: 155A. Sometimes some light yellow color (4D) diffused near midrib. Distal portion of apex between 147A and 146A. Most primary veins yellowish or light green. Distal portion of midrib darker green (varies between 146A and 146B). Mature spathe, back surface: 155A, except for an area near midrib, which is between 155A and 4D. Distal portion of apex between 147B and 146A. Midrib, slightly over 1 cm wide at juncture with stipe, is between 147A and 147B. Shortly above mid-length midrib tapers to about 2 mm and becomes more yellow. In the distal zone it is mostly 144A, except for 147A in the apex. A diffused yellow color (4C to 4D) is usually limited to a narrow band on each side of midrib, but sometimes extends outwardly. Most primary veins green, vary between 144A, 144B and 144C near midrib, much lighter near margin.

*Spadix.*—Shape: Cylindrical, slightly tapered towards apex; cross section approximately round. Size: About 12.6 cm long, about 2.5 cm in diameter. Flower density: About 5 to 6 flowers per linear 2 centimeters of spadix (mid-section). Color: Pistils 158B or between 158B and 158A. Perianth approximately 158D.

*Botanical flower.*—Perianth: Well visible between relatively thin pistils. Irregular shape. Pistil: Between ellipsoid and ovoid. About 8–9 mm long; about 3 mm in diameter; protrudes about 4 mm beyond perianth. Stigma relatively small. Stamens: About 3 mm long; cream color; flat; firmly pressed against pistil. Filament about 1 mm long and 1.2 mm wide. Anthers about 2 mm long and 1 mm wide. Pollen: Very rarely observed. Fragrance: Weak to moderate, somewhat unpleasant scent detectable in the morning.

Roots description: Main roots thick, fleshy, cream to light brown with yellow root caps. Abundant lateral roots.

Disease and insect resistance: Plants of 'Stwentynine', which are grown in commercial greenhouses and shadehouses, have not shown any unusual susceptibility to pathogens or insects common to Spathiphyllum.

I claim:

1. A new and distinct cultivar of Spathiphyllum plant named 'Stwentynine', as described and illustrated herein.

* * * * *